United States Patent [19]
Winter et al.

[11] Patent Number: 5,662,918
[45] Date of Patent: Sep. 2, 1997

[54] PHARMACEUTICAL AGENTS CONTAINING DIPHOSPHONIC ACIDS AND SALTS THEREOF

[75] Inventors: Gerhard Winter, Dossenheim; Bernhard Pichler, Ketsch; Heinrich Woog, Laudenbach; Werner Heller, Grunstadt, all of Germany

[73] Assignee: Boehringer Mannheim GmbH, Mannheim, Germany

[21] Appl. No.: 387,818

[22] PCT Filed: Aug. 19, 1993

[86] PCT No.: PCT/EP93/02217

§ 371 Date: Feb. 24, 1995

§ 102(e) Date: Feb. 24, 1995

[87] PCT Pub. No.: WO94/05297

PCT Pub. Date: Mar. 17, 1994

[30] Foreign Application Priority Data

Aug. 27, 1992 [DE] Germany ............ 42 28 552.6

[51] Int. Cl.$^6$ ............................................. A61F 2/02
[52] U.S. Cl. ............................................... 424/423
[58] Field of Search ................................. 424/423

[56] References Cited

U.S. PATENT DOCUMENTS

| | | | |
|---|---|---|---|
| 4,645,762 | 2/1987 | Biere et al. | 514/105 |
| 4,687,767 | 8/1987 | Bosies et al. | 514/89 |
| 4,902,679 | 2/1990 | Benedict et al. | 514/86 |

*Primary Examiner*—Carlos A. Azpuru
*Attorney, Agent, or Firm*—Nikaido, Marmelstein, Murray & Oram LLP

[57] ABSTRACT

The invention concerns pharmaceutical preparations that are stable on storage, which contain at least one diphosphonic acid and/or at least one physiologically acceptable salt of such an acid as the active substance.

22 Claims, 2 Drawing Sheets

PHARMACEUTICAL AGENTS CONTAINING DIPHOSPHONIC ACIDS AND SALTS THEREOF

This application is a 371 of PCT/EP93/02217.

The invention concerns well-tolerated injection solutions that are stable when stored in primary packaging made of glass and contain at least one diphosphonic acid or at least one physiologically acceptable salt of such an acid, processes for producing these solutions and the use of polyethylene glycols to stabilize these solutions.

Diphosphonic acids within the sense of the present invention are compounds which have already been introduced some time ago into therapeutic practice for the treatment of disorders of calcium metabolism.

These compounds are of particular interest for the treatment of hypercalcaemia and are used as active substances in therapeutic agents for the treatment of osteoporosis and in tumour osteolysis. The efficacy of disphosphonates (sodium etidronate, dichloromethylene-diphosphonate, aminohydroxypropane-, aminohydroxybutane- aminohydroxypentane-, aminohydroxyhexane- diphosphonate, and others) in inhibiting bone-reabsorption which is increased in an unnatural manner in many bone diseases such as e.g. Morbus Paget, in bone tumours, in bone metastases, in osteoporosis or in hyperparathyroidism, has already been known for a long time.

Diphosphonates as pharmaceutical agents are described for example in EP 0 170 228; EP 0 197 478; EP 0 224 751; EP 0 252 504; EP 0 252 505; EP 0 258 618; EP 0 350 002; EP 0 273 190; WO 90/00798.

Solid forms of administration for pharmaceutical agents containing diphosphonates in the form of preparations containing effervescents are described in DE 3 500 670.

Diphosphonic acids and salts thereof are in principle readily soluble in water and are usually quite stable substances with regard to temperature influences. In the production of injection solutions which had been adjusted to the pH value of blood (pH value 7.4), the solutions unexpectedly became turbid on longer storage despite the good solubility of the active substances. In addition it turned out that the content of active substance in the injection solutions in the glass vessels became continuously lower on storage over a long period of time even when the solutions did not yet exhibit any turbidity. The reasons for this reduction is the content of active substance are unclear.

Injection solutions are usually filled into primary packaging made of glass (e.g. ampoules, vials, ready-to-use syringes, carpoules) in which case the glass ampoules used for pharmaceutical purposes are usually composed of glasses of hydrolytic class I. The chemical stability of glass vessels for pharmaceutical use is assessed by determining soluble, mineral substances that are released into water under standardized conditions. In this process the contact of the water with the inner surface of the vessel or with powdered glass is stipulated. The hydrolytic resistance is determined by titrating the hydroxide ions that are formed in the solution. The glass vessels are classified into four types of glass according to their hydrolytic resistance. Glass of class I is composed of neutral glass with a high hydrolytic resistance due to the chemical composition of the glass as such. Glass of class II is usually composed of soda-lime-silicate glass and has a high hydrolytic resistance due to appropriate surface treatment. Glass of class III is usually composed of soda-lime-silicate glass and has a medium hydrolytic resistance. Glass of class IV is composed of soda-lime-silicate glass and has a low hydrolytic resistance.

Despite the use of glass containers of hydrolytic class I it was established that the content of aluminium ions in the injection solutions continuously increased on longer storage.

Due to these three disadvantageous findings on longer storage of the solutions—turbidities, reduction in the content of active substance and increase of the aluminium content—such solutions must be labelled as being physically unstable with regard to the intended official licence and registration as pharmaceutical agents. In addition it is also undesirable from a medical point of view to administer solutions when they have an increased aluminium content.

The object of the invention was therefore to provide injection solutions of diphosphonic acids or of their salts which are stable up to 5 years when stored in glass containers and which are well-tolerated when administered to humans.

It has now been found that injection solutions containing at least one diphosphonic acid or at least one acceptable salt or ester of such an acid that are stable in glass containers can be prepared when these solutions have a pH value between about 3.0 and 4.5 and/or contain polyethylene glycols and optionally are filled into glass containers that are surface treated.

Surprisingly aluminium concentrations are achieved that are less than 2 ppm, the content of active substances in the solution remains constant and no turbidities occur. The pH value of the solutions is preferably at about 4. The solutions are stable for up to 5 years on storage at room temperature. Moreover it was found that the solution of pharmaceutical agent is well-tolerated when administered intravenously despite the low pH value and is thus well-suited for administration to humans.

The addition of polyethylene glycols to the solution has the same effect as lowering the pH value. The polyethylene glycols that can be used usually have a molar weight between 100 and 1500, in particular of 200–600. Macrogol® is preferably used. FIG. 1 illustrates the reduction of the aluminium content of the solution when Macrogol® is added. The amount of added polyethylene glycols can be up to 20 volume percent. 5–10% of the polyethylene glycols is preferably used. In particular 1 ml injection solution contains 0.05 to about 0.2 ml Macrogol®.

An even stronger reduction of the aluminium content is achieved by combining both measures—reducing the pH value to about 3.0–4.5 and addition of polyethylene glycol (cf. FIG. 2).

The concentration of aluminium ions can be reduced further by filling the injection solution into the glass ampoules, if desired, under an inert gas atmosphere. For example gassing the solution with nitrogen during its production leads to comparable results. As a further measure to reduce the aluminium content, the surface of the glass container can be optionally treated. In the treatment a thin surface layer is produced on the inside of the ampoule glass by for example evaporation coating with ammonium sulfate, sulphur dioxide, sulphur trioxide or ammonium chloride.

The invention is described in the following on the basis of examples some of which are illustrated by diagrams. 1-Hydroxy-3-(N-methyl-N-pentyl)aminopropyl-1,1-diphosphonic acid (=A), dichloromethane-diphosphonic acid (=B, clodronate) and 3-amino-1-hydroxypropylidene-diphosphonic acid (=C, pamidronate) are used as active substances representing the group of diphosphonates in a suitable solution for injection. The active substance A is described in the European Application EP 0 252 505. In principle it is also possible to use other diphosphonic acids or physiologically acceptable salts thereof or physiologically acceptable esters thereof in a corresponding manner.

EXAMPLES 1 TO 9

Figure 1:
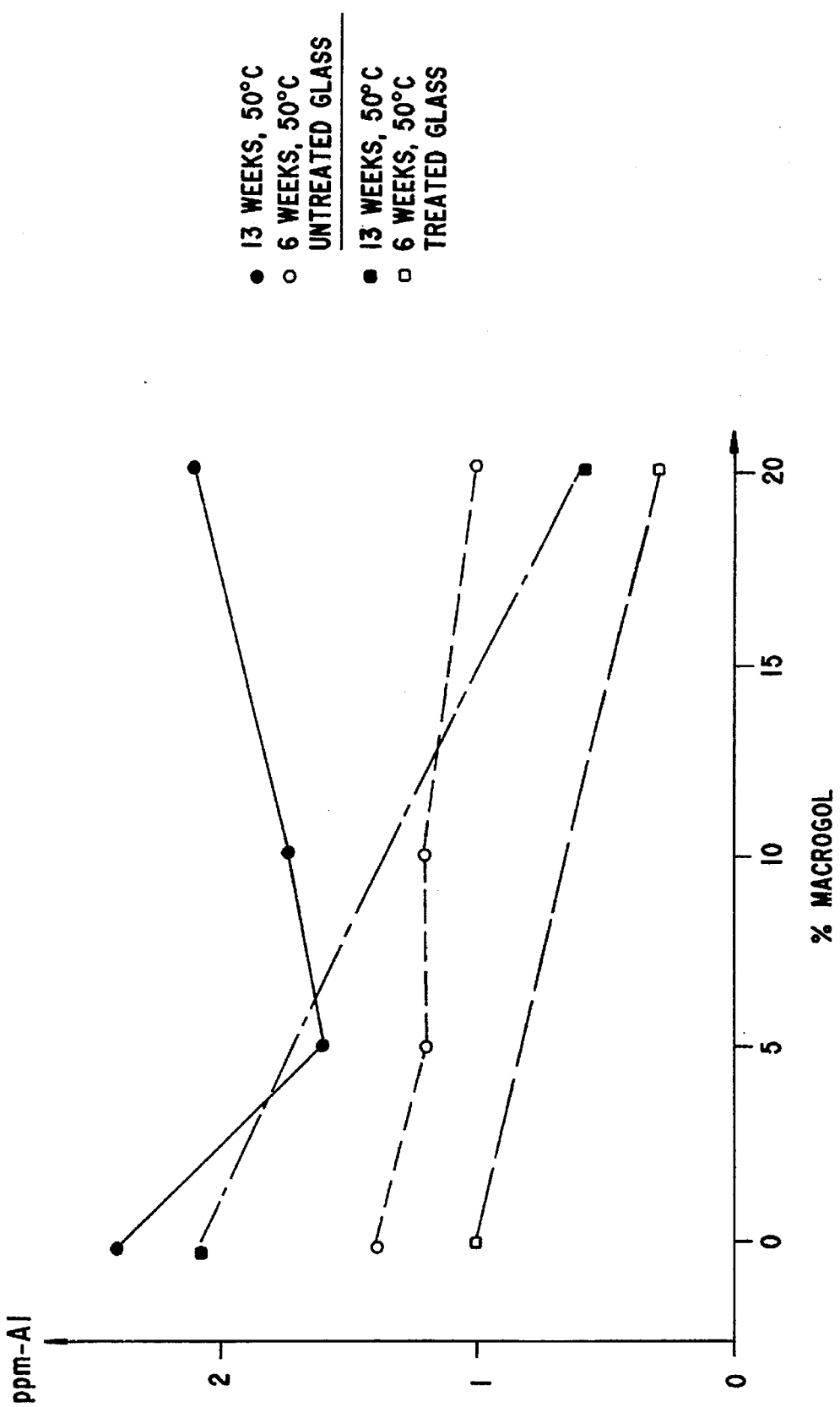
FIGS. 1 and 2 show diagrammatically the relationship between the aluminium content of the injection solutions described in examples 9 to 15 and the factors pH value, addition of auxiliary substance and storage time.

The injection solutions described in examples 1 to 9 contained in each case 1.069 mg sodium salt of 1-hydroxy-3-(N-methyl-N-pentyl)aminopropyl-1,1-diphosphonic acid and 8.6 mg NaCl per ml aqueous solution. The components or properties which were not identical in all solutions are listed in Table 1. The pH values were adjusted by adding appropriate amounts of NaOH or HCl. The solutions were filled into ampoules made of glass of hydrolytic class I. The solutions were sterilized for 20 minutes at 121° C. before storage. Before and after the sterilization and after a storage period of six weeks at 50° C., the aluminium content in the solutions was determined by means of AAS (atomic absorption spectroscopy). The aluminium values—averaged over 10 solution samples per example in each case—are also listed in Table 1.

TABLE 1

| Ex. No. | pH | $N_2$ gassing | Macrogol [mg/ml sol.] | Al content [ppm] before steril. | after steril. | after 6 weeks |
|---|---|---|---|---|---|---|
| 1 | 3 | | | 0.4 | 0.9 | 1.0 |
| 2 | 4 | | | 0.2 | 0.4 | 1.1 |
| 3 | 4.5 | | | 0.2 | 0.5 | 1.2 |
| 4 | 5 | | | 0.3 | 0.6 | 1.8 |
| 5 | 6 | | | 0.6 | 1.3 | 4.5 |
| 6 | 6 | + | | 0.4 | 0.8 | 4.6 |
| 7 | 6 | | 0.2 | 0.3 | 0.4 | 1.2 |
| 8 | 6 | | | 0.3 | 0.7 | 4.4[1] |
| 9 | 7 | | | 1.2 | 2.1 | 4.3 |

[1] Addition of propylene glycol (0.2 ml per 1 ml solution)

The results show that low pH values and/or the addition of a polyethylene glycol such as e.g. Macrogol (see example 7) are able to keep the aluminium content particularly low and that $N_2$ gassing during the production of the solution at least initially contributes to a lowered aluminium content of the solutions and that although the addition of other solvents with organic hydroxyl groups also reduces the aluminium content of the solution (see example 8), this is, however, much less than in the case of polyethylene glycols.

EXAMPLE 10 TO 16

The injection solutions described in examples 10 to 16 contained in each case 1.12 mg sodium salt of 1-hydroxy-3-(N-methyl-N-pentyl)aminopropyl-1,1-diphosphonic acid and 8.6 mg NaCl per ml aqueous solution. The solutions were gassed with nitrogen during their production. The components or properties which were not identical in all solutions are listed in Table 2. The pH value in example 16 was adjusted by adding an appropriate amount of NaOH. The solutions of examples 10 to 13 were filled into ampoules made of glass of hydrolytic class I and those of solutions 14 to 16 were filled into OPC ampoules the surface of which had been treated with ammonium sulfate. The solutions were sterilized for 20 minutes at 121° C. before storage. After sterilization and after storage periods of 6 and 13 weeks at 50° C., the aluminium content in the solutions was determined by means of AAS. The aluminium values—averaged over 10 solution samples per example in each case—are also listed in Table 2.

TABLE 2

| Ex. No. | treated glass | Macrogol [ml/ml sol.] | pH | Al content [ppm] before steril. | after 6 weeks | after 13 weeks |
|---|---|---|---|---|---|---|
| 10 | | | 4 | 0.5 | 1.4 | 2.4 |
| 11 | | 0.05 | 4 | 0.6 | 1.2 | 1.6 |
| 12 | | 0.10 | 4 | 0.7 | 1.2 | 1.7 |
| 13 | | 0.20 | 4 | 0.6 | 1.0 | 2.1 |
| 14 | + | | 4 | 0.1 | 1.0 | 2.1 |
| 15 | + | 0.20 | 4 | 0.1 | 0.3 | 0.6 |
| 16 | + | | 6 | 0.8 | 4.5 | 5.9 |

Figure 2:
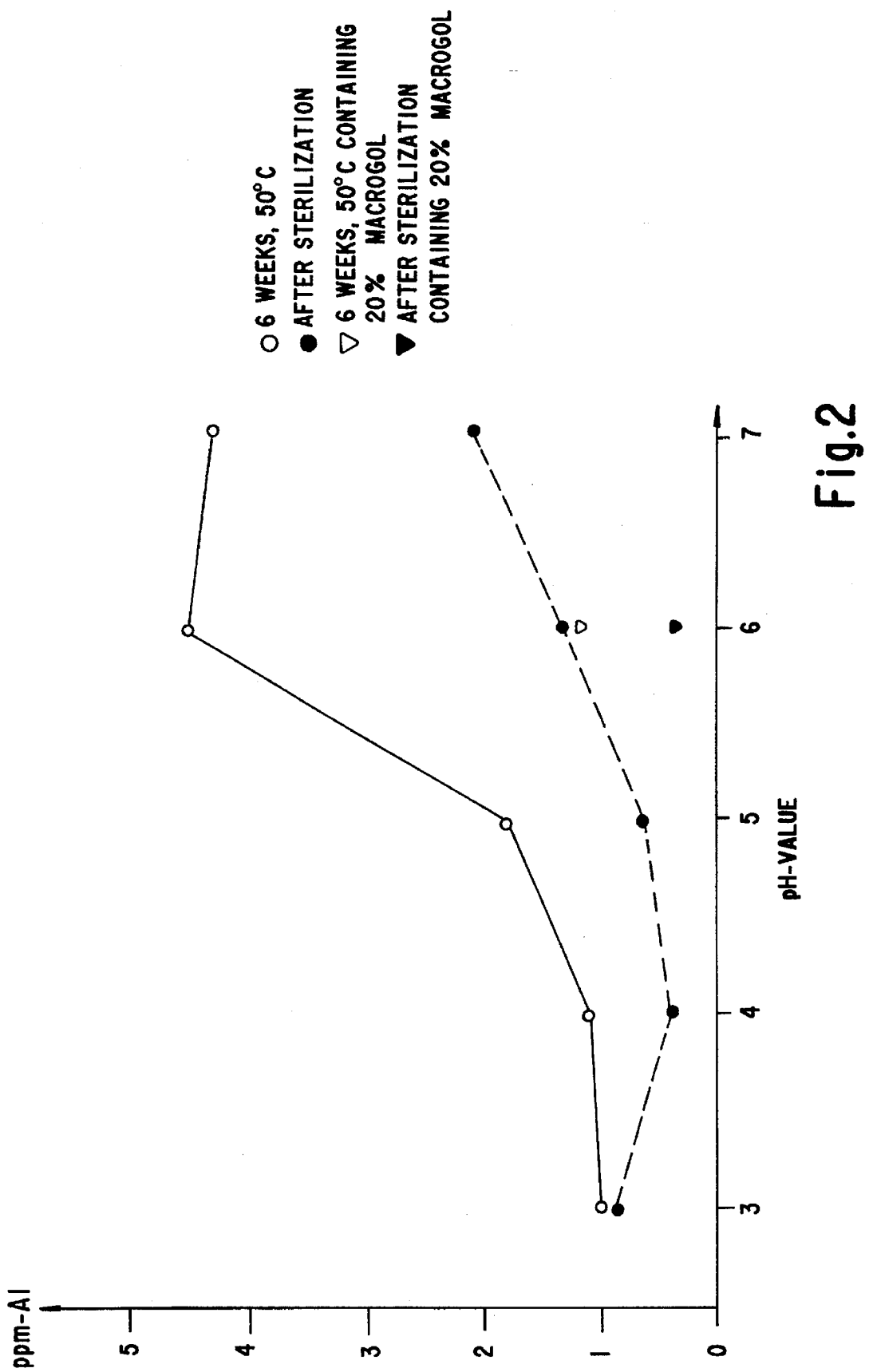

The aluminium values during the storage period of the solutions according to the invention described in examples 11 to 13 and 14 to 16 and in comparison to the aluminium values of the solution described in example 10 which only had $N_2$ gassing as the inventive feature as used in all examples of the second series to reduce the aluminium content in the injection solutions, are plotted in FIGS. 1 and 2.

The results show—similar to those achieved in the first series of examples—that Macrogol considerably reduces the aluminium content (see examples 11–13) and smaller amounts appear to be even more effective than larger amounts. They also show that treated glass alone (see example 14) or together with Macrogol (see example 15) forms a barrier against the dissolution of aluminium, but also that the effect of a high pH value cannot be blocked by treated glass (see example 16).

EXAMPLE 17

Investigations on the stability of solutions in relation to the pH value of the solutions.

The following active substances were used to prepare the injection solutions:

A=1-hydroxy-3-(N-methyl-N-pentyl)aminopropyl-1,1-diphosphonic acid; concentration: 1 mg/ml B=1,1-dichloro-1,1-diphosphonic acid, Na salt×4 $H_2O$; concentration: 300 mg/10 ml C=3-amino-1-hydroxypropylidene-diphosphonic acid; concentration: 3 mg/ml The aluminium determinations were carried out by AAS. The stated data are means of five or ten determinations. The injection solutions were prepared according to the following protocol: The active substance is dissolved in water for injection purposes and the desired pH value is adjusted with NaOH or HCl. In the case of the active substance B, the desired pH value is adjusted with sodium bicarbonate. The filling into ampoules is carried out under aseptic conditions after filtration over sterilized membrane filters of pore size 0.2 µm. Solutions containing active substances A and C were additionally sterilized at 121° C. Glass ampoules of hydrolytic class I were used.

TABLE 3

| Active substance | pH | Temp. [0° C.] | Storage period (month) | Al content [ppm] |
|---|---|---|---|---|
| — | 6 | 21–25 | 19 | 0.3 |
| A | 6 | 21–25 | 8 | 3.2 |
| A | 6 | 50 | 1.5 | 4.4 |
| A | 5 | 50 | 1.5 | 1.8 |
| A | 4 | 50 | 1.5 | 1.1 |
| A | 4 | 50 | 3 | 1.3 |
| A | 4 | 30 | 3 | 0.7 |
| A | 3 | 50 | 1.5 | 1.0 |
| B | 5.7 | 25 | 22 | 3.6 |
| B | 4.3 | 25 | 21 | 0.6 |
| C | 4.3 | 50 | 3 | 1.9 |
| C | 6.5 | 50 | 3 | 3.9 |

As can be seen in the above table the aluminium content of the injection solution increases when the solutions have a pH value which is near to the pH value of blood and when the solutions are stored under stress. The stronger stressing of the samples can be achieved by longer storage at room temperature or by storage at increased temperatures over a correspondingly shorter time period. Solutions which have a pH value of under 5 have a comparably lower aluminium content.

EXAMPLE 18

The injection solutions described in example 18 contain in each case 3 mg Pamidronate=APD=3-amino-hydroxypropylidene-bisphosphonic acid per ml aqueous solution. In the production of the solutions the pH value is adjusted to 4, 5, 6 with small amounts of NaOH. In each case 1 ml of the solutions was filled into 1 ml glass ampoules of hydrolytic class I. The ampoules were stored at room temperature (21°–25° C.) and at 50° C. and then the aluminium content in the solutions was determined by means of AAS. The means of 5 measurements in each case are shown in Table 4 in relation to the storage temperature and pH. It is clear from the data that lowering the pH value from 6 to 5 or 4 decreases the aluminium contents to ca. 50%.

TABLE 4

Aluminium ions in glass ampoules containing Pamidronate (APD) 3 mg/1 ml injection solution

| pH value of the injection solution | Storage period (weeks) | Temperature stress | Al content (ppm) per ampoule mean of 5 measurements |
|---|---|---|---|
| 4 | 8 | RT | 0.46 |
| 4 | 8 | RT | 0.46 |
| 4 | 8 | 50° C. | 0.72 |
| 4 | 8 | 50° C. | 0.84 |
| 5 | 8 | RT | 0.54 |
| 5 | 8 | RT | 0.47 |
| 5 | 8 | 50° C. | 1.00 |
| 5 | 8 | 50° C. | 0.65 |
| 6 | 8 | RT | 0.80 |
| 6 | 8 | RT | 0.75 |
| 6 | 8 | 50° C. | 1.68 |
| 6 | 8 | 50° C. | 1.40 |

RT = room temperature

EXAMPLE 19

The injection solutions described in example 19 contain in each case 1.069 mg sodium salt of 1-hydroxy-3-(N-methyl-N-pentyl)aminopropyl-1,1-diphosphonic acid and 8.6 mg NaCl per ml aqueous solution. The pH value was adjusted with 0.5 mg acetic acid and 0.2 mg sodium acetate (3 $H_2O$). The solutions were filled into glass ampoules of hydrolytic class I and sterilized for 20 minutes at 121° C. before storage.

After an appropriate storage period the aluminium content in the solution was determined by means of AAS. The results are shown in Table 5. All solutions were clear after storage and had the complete amount of active substance. The tolerance of these preparations after i.v. injection was very good.

| Injection solution No. | Storage period (weeks) | Temperature stress °C. | pH value of the injection solution | Al content (ppm) per ampoule mean of 5 measurements |
|---|---|---|---|---|
| 19.1 | 52 | 6–8 | 3.9 | 0.47 |
| 19.1 | 52 | 25 | 3.9 | 0.6 |
| 19.1 | 52 | 30 | 4.0 | 0.73 |
| 19.2 | 52 | 6–8 | 4.3 | 0.58 |
| 19.2 | 52 | 25 | 4.3 | 1.0 |
| 19.2 | 52 | 30 | 4.3 | 1.18 |
| 19.3 | 52 | 6–8 | 4.1 | 0.13 |
| 19.3 | 52 | 25 | 4.1 | 0.16 |
| 19.3 | 52 | 30 | 4.1 | 0.28 |
| 19.4 | 52 | 6–8 | 4.3 | 0.39 |
| 19.4 | 52 | 25 | 4.3 | 0.63 |
| 19.4 | 52 | 30 | 4.3 | 0.77 |

We claim:

1. Injection solution which is stable on storage in a glass container, said solution being an aqueous solution containing at least one bone-reabsorption-inhibiting diphosphonic acid or physiologically acceptable salt or ester thereof as the active substance, said solution being stabilized by having a pH value of the solution of about 3.0 to 4.5 or by having a pH value of the solution of about 3.0 to 4.2 and the presence of polyethylene glycols.

2. Solution of claim 1, wherein the pH value of the solution is of about 3.0 to 4.5 and the solution contains polyethylene glycols.

3. Solution of claim 1, wherein the pH value of the solution is about 4.

4. Solution of claim 1, wherein the solution contains up to 20% of polyethylene glycols having a molecular weight of about 200–1500.

5. Solution of claim 4, wherein the solution contains about 0.05 to about 0.2 ml of polyethylene glycols per 1 ml of injection solution.

6. Solution of claim 1, wherein the solution contains at least one 1-hydroxy-aminoalkyl-1,1-diphosphonic acid or physiologically acceptable salt or ester thereof as the active substance.

7. Solution of claim 6, wherein the active substance is 1-hydroxy-3-(N-methyl-N-pentyl) aminopropyl-1,1-diphosphonic acid or physiologically acceptable salt thereof.

8. Solution of claim 1, wherein the active substance is in the form of a pharmaceutically acceptable alkali salt.

9. Solution of claim 1, wherein the solution contains the active substance in an amount of about 0.1 to about 1000 mg and NaCl in an amount of less than 10 mg/ml of aqueous solution.

10. A kit comprising a glass container containing an aqueous injection solution of at least one physiologically acceptable bone-reabsorption-inhibiting diphosphonic acid or salt or ester thereof as the active ingredient, said solution being stable on storage in the container for up to 5 years, said solution having a pH value of about 3.0–4.5.

11. A kit comprising a glass container containing one physiologically acceptable bone-reabsorption-inhibiting diphosphonic acid or salt or ester thereof as the active ingredient, said solution being stable on storage in the container for up to 5 years, said solution containing polyethylene glycols and having a pH value of about 3.0–4.5.

12. A method for stabilizing an aqueous injection solution for the treatment of bone diseases, said solution being storage stable for up to 5 years and containing as the active substance at lease one bone-reabsorption-inhibiting diphosphonic acid or physiologically acceptable salt or ester thereof, said solution being stored in a glass container, said method comprising adjusting the pH Value of the solution to about 3.0–4.5 prior to filling the glass container with the solution.

13. A method for stabilizing an aqueous injection solution for the treatment of bone diseases, said solution being storage stable for up to 5 years and containing as the active substance at lease one bone-reabsorption-inhibiting diphosphonic acid or physiologically acceptable salt or ester thereof, said solution being stored in a glass container, said method comprising adjusting the pH to about 3.0 to 4.5 and adding polyethylene glycols to the solution.

14. Method of claim 12, wherein the glass container has been surface-treated before being filled by the solution.

15. Method of claim 12, wherein the pH value is adjusted to about 4.0.

16. Method of claim 13, wherein the glass container has been surface-treated before being filled by the solution.

17. Method of claim 13, wherein the pH value is adjusted to about 4.0.

18. Solution of claim 1, wherein the solution is stabilized by having a pH value of 3 to 4.5, and the solution is free of polyethylene glycols.

19. The kit of claim 10 wherein the glass container has been surface treated.

20. The kit of claim 19 wherein the glass container has been surface treated with ammonium sulfate, sulfur dioxide, sulfur trioxide or ammonium chloride.

21. The kit of claim 11 wherein the glass container has been surface treated.

22. The kit of claim 21 wherein the glass container has been surface treated with ammonium sulfate, sulfur dioxide, sulfur trioxide or ammonium chloride.

* * * * *